US00PP33083P2

(12) United States Plant Patent
van der Meer

(10) Patent No.: US PP33,083 P2
(45) Date of Patent: May 18, 2021

(54) ***ASTILBE* PLANT NAMED 'LUCY'**

(50) Latin Name: *Astilbe arendsii*
Varietal Denomination: Lucy

(71) Applicant: Hans van der Meer, Nieuwe Wetering (NL)

(72) Inventor: Hans van der Meer, Nieuwe Wetering (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/974,009

(22) Filed: Sep. 5, 2020

(51) Int. Cl.
*A01H 6/80* (2018.01)
*A01H 5/02* (2018.01)

(52) U.S. Cl.
USPC ..... Plt./407

(58) Field of Classification Search
USPC ..... Plt./407
See application file for complete search history.

*Primary Examiner* — Annette H Para
(74) *Attorney, Agent, or Firm* — C. Anne Whealy

(57) ABSTRACT

A new and distinct cultivar of *Astilbe* plant named 'Lucy', characterized by its compact, broadly upright and mounding plant habit; vigorous growth habit; dark green-colored leaves; freely and uniformly flowering habit; purplish red-colored flowers arranged in compact inflorescences and borne on red-colored, upright and strong peduncles; and good container and garden performance.

2 Drawing Sheets

Botanical designation: *Astilbe arendsii.*
Cultivar denomination: 'LUCY'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Astilbe*, botanically known as *Astilbe arendsii* and hereinafter referred to by the name 'Lucy'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from an open-pollination in 2014 in Nieuwe Wetering, The Netherlands, of an unnamed proprietary selection of *Astilbe arendsii*, not patented, as the female, or seed, parent with an unknown *Astilbe arendsii* seedling selection as the male, or pollen, parent. The new *Astilbe* plant was discovered and selected by the Inventor as a single flowering plant from within the progeny of the stated open-pollination in a controlled greenhouse environment in Nieuwe Wetering, The Netherlands during the summer of 2015.

Asexual reproduction of the new *Astilbe* plant by vegetative divisions in a controlled nursery environment in Nieuwe Wetering, The Netherlands since December, 2015, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lucy'. These characteristics in combination distinguish 'Lucy' as a new and distinct *Astilbe* plant:

1. Compact, broadly upright and mounding plant habit.
2. Vigorous growth habit.
3. Dark green-colored leaves.
4. Freely and uniformly flowering habit.
5. Purplish red-colored flowers arranged in compact inflorescences and borne on red-colored, upright and strong peduncles.
6. Good container and garden performance.

Plants of the new *Astilbe* differ primarily from plants of the female parent selection in the following characteristics:

1. Plants of the new *Astilbe* are more compact than plants of the female parent selection.
2. Plants of the new *Astilbe* are more freely flowering than plants of the female parent selection.
3. Flowers of plants of the new *Astilbe* are darker purplish red than flowers of plants of the female parent selection.
4. Inflorescences of plants of the new *Astilbe* are more compact than inflorescences of plants of the female parent selection.

Plants of the new *Astilbe* can be compared to plants of *Astilbe arendsii* 'Lara', not patented. In side-by-side comparisons, plants of the new *Astilbe* and 'Lara' differ primarily in the following characteristics:

1. Plants of the new *Astilbe* are more compact than plants of 'Lara'.
2. Plants of the new *Astilbe* are more freely flowering than plants of 'Lara'.
3. Flowers of plants of the new *Astilbe* are purplish red in color whereas flowers of plants of 'Lara' are pink in color.
4. Inflorescences of plants of the new *Astilbe* are smaller and denser than inflorescences of plants of 'Lara'.
5. Peduncles of plants of the new *Astilbe* are red in color whereas peduncles of plants of 'Lara' are green in color

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet is a side perspective view of a typical flowering plant of 'Lucy' grown in a container.

The photograph on the second sheet is a close-up view of typical inflorescences of 'Lucy'.

DETAILED BOTANICAL DESCRIPTION

The aforementioned photographs and following observations, measurements and values describe plants grown during the spring and early summer in ground beds and 30-cm containers in an outdoor nursery in Nieuwe Wetering, The Netherlands and under cultural practices typical of commercial *Astilbe* production. During the production of the plants, day temperatures ranged from 15° C. to 27° C. and night temperatures ranged from 5° C. to 18° C. Plants were two years old when the photographs and description were taken. In the following description, color references are made to The Royal Horticultural Society Colour Chart, 2015 Edition, except where general terms of ordinary dictionary significance are used.

Botanical classification: *Astilbe arendsii* 'Lucy'.

Parentage:

*Female, or seed, parent*.—Unnamed proprietary selection of *Astilbe arendsii*, not patented.

*Male, or pollen, parent*.—Unknown *Astilbe arendsii* seedling selection, not patented.

Propagation:

*Type*.—By vegetative divisions.

*Time to initiate roots*.—About three weeks at temperatures about 20° C.

*Root description*.—Thick, fleshy; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial; compact, broadly upright and mounding plant form with inflorescences held slightly above the foliar plane; flowering stems and leaves basal; freely flowering with about 24 basal branches per plant, dense and bushy; vigorous growth habit; and freely and uniformly flowering habit.

*Growth rate*.—Moderately rapid; from divisions, about three months are required to produce fully-grown flowering plants in containers.

*Plant height* (*soil level to top of foliar plane*).—About 29 cm.

*Plant height* (*soil level to top of inflorescences*).—About 43.1 cm.

*Plant width* (*spread*).—About 49.3 cm.

*Stem description*.—Length: About 25.3 cm. Diameter: About 3 mm. Internode length: About 8 cm. Strength: Strong. Aspect: Erect to about 5° from vertical. Texture and luster: Smooth, glabrous; glossy. Color, developing: Close to 152D; surfaces exposed to sunlight, moderately tinged with close to 165A. Color, developed: Close to 176A; surfaces exposed to sunlight, strongly tinged with close to between 46A and 181A.

Leaf description:

*Arrangement*.—Alternate; biternately compound; on average, about 25 leaflets per leaf.

*Leaf length* (*excluding petiole*).—About 11.8 cm.

*Leaf width*.—About 12.7 cm.

*Terminal leaflet length*.—About 5.1 cm.

*Terminal leaflet width*.—About 2.1 cm.

*Lateral leaflet length*.—About 3.7 cm.

*Lateral leaflet width*.—About 1.6 cm.

*Leaf shape, in outline*.—Broadly ovate to broadly rhomboidal.

*Leaflet shape*.—Narrowly elliptic to narrowly ovate.

*Leaflet apex*.—Acute.

*Leaflet base*.—Truncate to obtuse.

*Leaflet margin*.—Biserrate.

*Leaflet texture and luster, upper surface*.—Sparsely pubescent; moderately glossy.

*Leaflet texture and luster, lower surface*.—Sparsely pubescent; slightly glossy.

*Leaflet venation pattern*.—Pinnate.

*Leaflet color*.—Developing leaflets, upper surface: Slightly more green than 146A. Developing leaflets, lower surface: Close to 146B. Fully expanded leaflets, upper surface: Close to NN137B; venation, close to 145B. Fully expanded leaflets, lower surface: Close to between 137B and 147B; venation, close to 152D.

*Leaf petiole length*.—About 14.7 cm.

*Leaf petiole diameter*.—About 2 mm.

*Leaf and leaflet petiole strength*.—Strong.

*Leaf and leaflet petiole texture and luster, upper and lower surfaces*.—Mostly smooth and glabrous, proximally, sparsely pubescent; moderately glossy.

*Leaf and leaflet petiole color, upper surface*.—Close to 152C strongly tinged with close to 178B.

*Leaf and leaflet petiole color, lower surface*.—Close to 152D moderately tinged with close to 178D.

Flower description:

*Flower type and flowering habit*.—Single rotate flowers arranged on terminal compound panicles; flowers face upright, outward or downward depending on position on the inflorescence; panicles conical in shape; freely and uniformly flowering habit with about 1,750 flowers developing per inflorescence and about 42,000 flowers developing per plant during the flowering season.

*Fragrance*.—Strong; moldy-sweet and pleasant.

*Natural flowering season*.—Plants begin flowering about 13 weeks after planting; continuously flowering from late spring until late summer in The Netherlands.

*Postproduction longevity*.—Flowers last about ten days on the plant; flowers not persistent.

*Flower buds*.—Height: About 2 mm. Diameter: About 1.25 mm. Shape: Broadly elliptic. Texture and luster: Smooth, glabrous; matte. Color: Sepals, close to 148C and petals, close to 60B.

*Inflorescence height*.—About 17.1 cm.

*Inflorescence diameter*.—About 9.5 cm.

*Flower diameter*.—About 9 mm.

*Flower depth*.—About 4 mm.

*Petals*.—Quantity per flower: Typically five in a single whorl. Length: About 5 mm. Width: About 0.8 mm. Shape: Oblanceolate. Apex: Obtuse. Base: Narrowly cuneate. Margin: Entire; not undulate. Texture and luster, upper and lower surfaces: Smooth, glabrous; matte. Color: Developing petals, upper and lower surfaces: Close to 61C. Fully expanded petals, upper and lower surfaces: Close to 61B; venation, close to 61B; color becoming closer to 61C with development.

*Sepals*.—Calyx length: About 1.5 mm. Calyx diameter: About 2 mm. Quantity per flower: Typically five in a single whorl, lower 40% fused towards the base forming a campanulate-shaped calyx. Length: About 1.5 mm. Width: About 0.7 mm. Shape: Ovate. Apex: Bluntly acute. Base: Cuneate, fused. Margin: Entire. Texture and luster, upper and lower surfaces: Smooth, glabrous; matte. Color: Developing sepals, upper and lower surfaces: Close to 59D tinged with close to 148C; margins, close to 46B. Fully developed sepals, upper and lower surfaces: Close to 59D tinged with close to 148C; margins, close to 46B.

*Peduncles*.—Length: About 16.8 cm. Diameter: About 1.5 mm. Angle: Mostly erect; secondary peduncles, about 35° from primary peduncle axis. Strength: Strong. Texture and luster: Moderately pubescent; moderately glossy. Color: Close to 181A.

*Pedicels*.—Length: About 1 mm. Diameter: About 0.5 mm. Angle: About 40° from peduncle axis. Strength: Moderately strong. Texture and luster: Sparsely pubescent; matte. Color: Close to 60A.

*Reproductive organs*.—Stamens: Quantity per flower: Typically ten. Filament length: About 3 mm. Filament color: Close to 61B. Anther shape: Broadly ovate; basifixed. Anther length: About 0.5 mm. Anther diameter: About 0.25 mm. Anther color: Close to 186C. Pollen amount: Scarce. Pollen color: Close to 156D. Pistils: Quantity per flower: Two. Pistil length: About 1.5 mm. Stigma diameter: About 0.1 mm. Stigma shape: Club-shaped. Stigma color: Close to 63D. Style length: About 1 mm. Style color: Close to 59B. Ovary color: Close to 59B to 59C.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25° to 35° C. and to be suitable for USDA Hardiness Zones 5 through 10.

It is claimed:

1. A new and distinct *Astilbe* plant named 'Lucy' as illustrated and described.

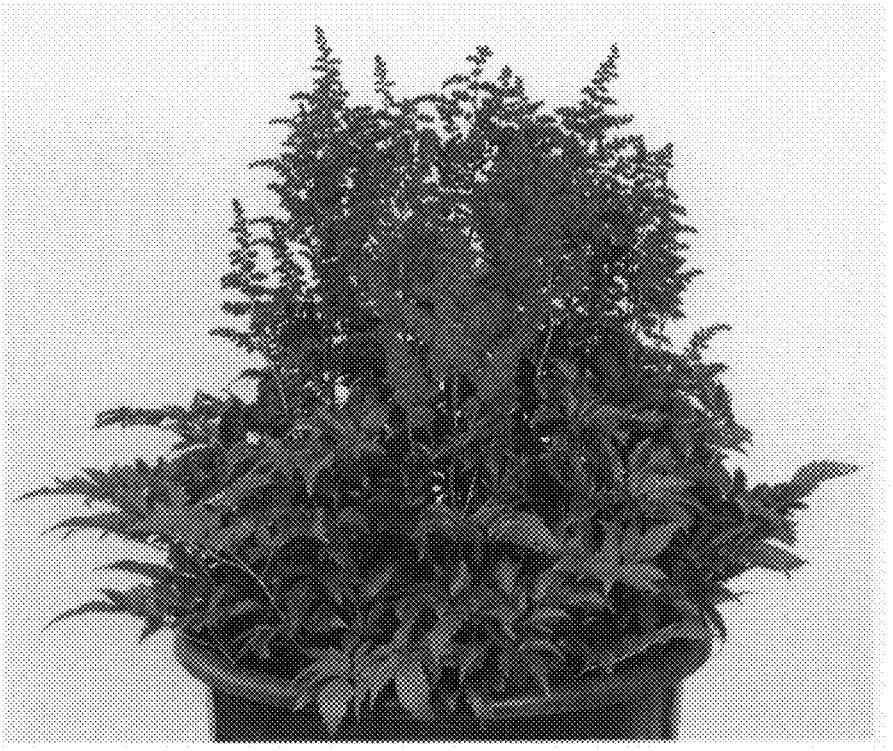

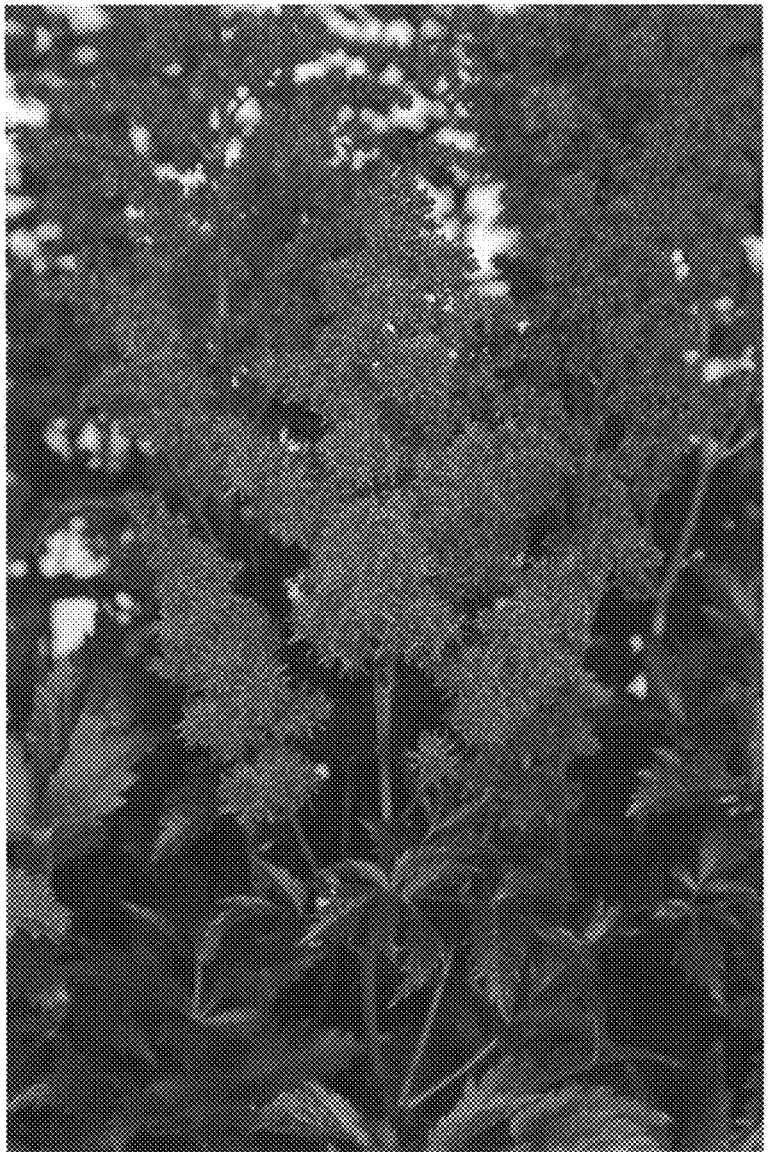

* * * * *